(12) United States Patent
Wagner et al.

(10) Patent No.: US 6,262,091 B1
(45) Date of Patent: Jul. 17, 2001

(54) PROCESS AND AGENTS FOR CONTROLLING HARMFUL FUNGI

(75) Inventors: Oliver Wagner, Ludwigshafen; Karl Eicken, Wachenheim; Eberhard Ammermann, Heppenheim; Gisela Lorenz, Hambach; Siegfried Strathmann, Limburgerhof; Harald Köhle, Bobenheim; Günter Retzlaff, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/171,523

(22) PCT Filed: Apr. 22, 1997

(86) PCT No.: PCT/EP97/02036
§ 371 Date: Oct. 21, 1998
§ 102(e) Date: Oct. 21, 1998

(87) PCT Pub. No.: WO97/39628
PCT Pub. Date: Oct. 30, 1997

(30) Foreign Application Priority Data

Apr. 22, 1996 (DE) .................................................. 19615977

(51) Int. Cl.[7] ........................ A01N 37/24; A01N 43/78; A01N 43/76; A01N 43/56; A01N 43/32; A01N 43/16; A01N 43/08; A01N 37/22; A01N 37/18

(52) U.S. Cl. ........................ 514/355; 514/519; 514/520; 514/521; 514/523; 514/525; 514/613; 514/617; 514/618; 514/623; 514/624; 514/354; 504/100; 422/28; 422/37

(58) Field of Search .................. 514/613, 617–625, 514/627–630, 354, 374, 378, 383, 406, 407, 519–521, 523, 525, 355; 504/100; 422/28, 37

(56) References Cited

U.S. PATENT DOCUMENTS

| | | | |
|---|---|---|---|
| 4,840,959 | 6/1989 | Oda et al. | 514/355 |
| 5,059,623 | 10/1991 | Krueger et al. | 514/613 |
| 5,223,526 * | 6/1993 | McLoughlin et al. | 514/406 |
| 5,330,995 * | 7/1994 | Eicken et al. | 514/355 |
| 5,438,070 * | 8/1995 | Eicken et al. | 514/403 |
| 5,532,262 | 7/1996 | Brandes et al. | 514/388 |
| 5,534,653 * | 7/1996 | Wagner et al. | 564/32 |
| 5,589,493 | 12/1996 | Eicken et al. | 514/355 |
| 5,962,518 * | 10/1999 | Stenzel et al. | 514/491 |
| 6,143,745 * | 11/2000 | Eicken et al. | 514/247 |
| 6,159,992 * | 12/2000 | Müller et al. | 514/355 |
| 6,169,056 * | 1/2001 | Bayer et al. | 504/118 |

FOREIGN PATENT DOCUMENTS

| | | |
|---|---|---|
| 2195577 | 2/1996 | (CA) . |
| 4437048 | 10/1994 | (DE) . |
| 19504599 | 8/1996 | (DE) . |

* cited by examiner

*Primary Examiner*—John Pak
(74) *Attorney, Agent, or Firm*—Keil & Weinkauf

(57) ABSTRACT

Compositions for controlling harmful fungi, containing in a solid or liquid carrier a) at least one p-hydroxyaniline derivative of the formula I

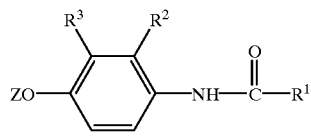

(I)

b) at least one amide compound of the formula II $$A—CO—NR^8—R^9 \quad \text{(II)}$$

where the substituents have the meanings indicated in the description;

and methods of controlling harmful fungi using compositions of this type are described.

19 Claims, No Drawings

PROCESS AND AGENTS FOR CONTROLLING HARMFUL FUNGI

This application is a 371 of ACT/EP97/02030, filed on Apr. 22, 1997.

TECHNICAL FIELD

The present invention relates to compositions for controlling harmful fungi and methods for controlling harmful fungi using compositions of this type.

BACKGROUND ART

It is known that p-hydroxyaniline derivatives of the formula I

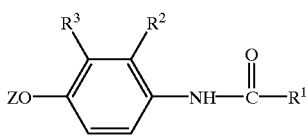

are employed as active compounds in fungicidal compositions. Thus compounds of the formula I are disclosed in EP-A 0 339 481, EP-A 0 653 418 and the German Patent Applications 195 04 599.8 and 95 40 970.1.

EP-A-545 099 describes anilide compounds of the formula

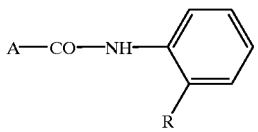

where A is phenyl which is substituted in the 2-position by ethyl, trifluoromethyl, chlorine, bromine or iodine or is certain aromatic or nonaromatic heterocyclic radicals, which can be unsubstituted or substituted by methyl, chlorine or trifluoromethyl, and R is certain aliphatic or cycloaliphatic radicals, which can be unsubstituted or substituted by halogen, or is phenyl which is unsubstituted or substituted by $C_1$–$C_4$-alkyl, $C_1$–$C_4$-alkoxy, $C_1$–$C_4$-alkylthio or halogen. These compounds can be used for controlling Botrytis.

EP-A-589 301 describes anilide compounds of the same formula, where A is a cyclic radical of the formula:

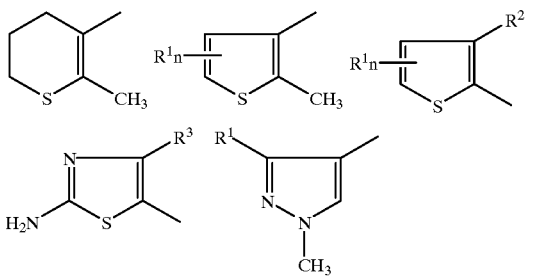

where $R^1$ is hydrogen or $C_1$–$C_4$-alkyl; $R^2$ is halogen or $C_1$–$C_4$-alkyl; $R^3$ is $C_1$–$C_4$-alkyl or $C_1$–$C_4$-haloalkyl; n is 1 or 2; and R essentially has the meanings indicated above. These compounds can also be used for treating Botrytis.

WO 93/11117 describes compounds of the formula

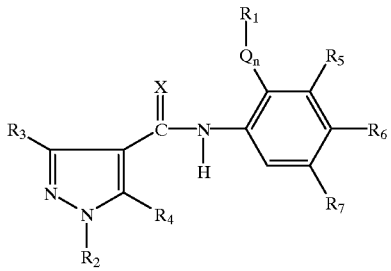

where

Q is $C_1$–$C_3$-alkyl, $C_2$–$C_3$-alkenyl, $C_2$–$C_3$-alkynyl, —$(CH_2)_m$CH= or —$(CH_2)_m$—X—$(CH_2)_m$—;

n is 0 or 1;

each m independently of one another is 0, 1, 2 or 3;

each X independently is O or S;

$R^1$ is certain alicyclic radicals;

$R^2$ is hydrogen, fluorinated methyl, methyl, ethyl, $C_2$–$C_6$-alkenyl, $C_3$–$C_6$-chloroalkyl, phenyl, alkylthioalkyl, alkoxyalkyl, haloalkylthioalkyl, haloalkoxyalkyl or hydroxyalkyl;

$R^3$ is halomethyl, halomethoxy, methyl, ethyl, halogen, cyano, methylthio, nitro, aminocarbonyl or aminocarbonylmethyl;

$R^4$ is hydrogen, halogen or methyl;

$R^5$, $R^6$ and $R^7$ are each independently of one another selected from hydrogen, halogen, cyano, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_3$–$C_4$-cycloalkyl and halomethoxy. These compounds are fungicidally active, but on their own do not have a sufficiently broad and satisfactory spectrum of action.

When these active compounds are used alone, however, it has been shown that their action is only temporary, i.e. after some time renewed growth of the fungi could be observed.

DISCLOSURE OF INVENTION

It is an object of the present invention to improve the action of the mentioned compounds in controlling harmful fungi.

We have found that this object is achieved if compounds of the type indicated are used in combination.

The invention therefore relates to compositions for controlling harmful fungi, which, in a solid or liquid carrier, contain:

a) at least one p-hydroxyaniline derivative of the formula I

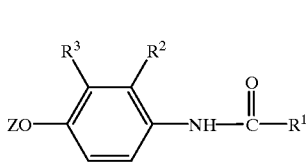

where $R^1$ is hydrogen, alkyl, which can be partially or completely halogenated and/or can carry one or two of the following groups: alkoxy, haloalkoxy, alkylthio, cycloalkyl, cycloalkenyl, it being possible for the cyclic groups for their part to carry one, two or three halogen atoms, alkyl groups and/or alkoxy groups, and aryl which can be partially or completely halogenated and/or can carry one, two or three of the following substituents: nitro, cyano, alkyl, haloalkyl, alkoxy, haloalkoxy and alkylthio;

cycloalkyl or cycloalkenyl, it being possible for these radicals to be partially or completely halogenated and/or to carry 1, 2, 3, 4 or 5 of the following groups: alkyl, haloalkyl, alkoxy, haloalkoxy and aryl, which can be partially or completely halogenated and/or can carry one, two or three of the following substituents: nitro, cyano, alkyl, haloalkyl, alkoxy, haloalkoxy and alkylthio;

$C_6$–$C_{15}$-bicycloalkyl or $C_7$–$C_{15}$-bicycloalkenyl, it being possible for these radicals to be partially or completely halogenated and/or to carry 1, 2, 3, 4 or 5 of the following groups: alkyl, haloalkyl, alkoxy, haloalkoxy and aryl, which can be partially or completely halogenated and/or can carry one, two or three of the following substituents: nitro, cyano, alkyl, haloalkyl, alkoxy, haloalkoxy and alkylthio;

$R^2$ and $R^3$ independently of one another are halogen, alkyl, haloalkyl, alkoxy or haloalkoxy;

z is H or $R^4$—(CO)—, where $R^4$ is the following radicals: alkyl or alkenyl, it being possible for these groups to be partially or completely halogenated and/or to carry one of the following radicals: alkoxy, haloalkoxy, alkylthio, cycloalkyl, cycloalkenyl or aryl, it being possible for the aromatic radicals for their part to carry one, two or three of the following groups: nitro, cyano, halogen, alkyl, haloalkyl, alkoxy, haloalkoxy and alkylthio;

cycloalkyl or cycloalkenyl, it being possible for these groups to carry one, two or three of the following radicals: halogen, alkyl, haloalkyl and alkoxy;

aryl, which can be partially or completely halogenated and/or can carry one, two or three of the following radicals: nitro, cyano, alkyl, haloalkyl, alkoxy, haloalkoxy and alkylthio;

$OR^5$ or $NR^6R^7$, where $R^5$ is alkyl or alkenyl, it being possible for these groups to be partially or completely halogenated and/or to carry one of the following radicals: alkoxy, haloalkoxy, alkylthio, cycloalkyl, cycloalkenyl or aryl, it being possible for the aromatic radicals for their part to carry one, two or three of the following groups: nitro, cyano, halogen, alkyl, haloalkyl, alkoxy, haloalkoxy and alkylthio;

or is cycloalkyl or cycloalkenyl, it being possible for these groups to carry one, two or three of the following radicals: halogen, alkyl, haloalkyl and alkoxy;

or is aryl which can be partially or completely halogenated and/or can carry one, two or three of the following radicals; nitro, cyano, alkyl, haloalkyl, alkoxy, haloalkoxy and alkylthio;

$R^6$ is alkyl or alkenyl, it being possible for these groups to be partially or completely halogenated and/or to carry one of the following radicals: alkylthio, cycloalkyl, cycloalkenyl or aryl, it being possible for the aromatic radicals for their part to carry one, two or three of the following groups: nitro, cyano, halogen, alkyl, haloalkyl, alkoxy, haloalkoxy and alkylthio;

cycloalkyl or cycloalkenyl, it being possible for these groups to carry one, two or three of the following radicals: halogen, alkyl, haloalkyl and alkoxy;

aryl, which can be partially or completely halogenated and/or can carry one, two or three of the following radicals: nitro, cyano, alkyl, haloalkyl, alkoxy, haloalkoxy and alkylthio; and $R^7$ is hydrogen or alkyl, and b) at least one amide compound of the formula II $$A\text{—}CO\text{—}NR^8\text{—}R^9 \qquad (II)$$

where

A is an aryl group or an aromatic or nonaromatic, 5- or 6-membered heterocycle which has 1 to 3 heteroatoms which are selected from O, N and S; it being possible for the aryl group or the heterocycle, if appropriate, to have 1, 2 or 3 substituents which are selected independently of one another from alkyl, halogen, $CHF_2$, $CF_3$, alkoxy, haloalkoxy, alkylthio, alkylsulfinyl and alkylsulfonyl;

$R^8$ is a hydrogen atom, alkyl or alkoxy;

$R^9$ is a phenyl or cycloalkyl group which, if appropriate, has 1, 2 or 3 substituents which independently of one another are selected from phenyl, alkenyl, alkynyl, alkenyloxy, alkynyloxy, cycloalkyl, cycloalkenyl, cycloalkyloxy and cycloalkenyloxy, and which can additionally be substituted by 1 or more halogen atoms, it being possible for the aliphatic and cycloaliphatic radicals to be partially or completely halogenated and/or the cycloaliphatic radicals to be substituted by 1, 2 or 3 alkyl groups and for the phenyl group for its part to have 1 to 5 halogen atoms and/or 1 to 3 substituents which independently of one another are selected from alkyl, haloalkyl, alkoxy, haloalkoxy, alkylthio and haloalkylthio, and the amide phenyl group, if appropriate, being fused to a saturated 5-membered ring which, if appropriate, is substituted by 1 or more alkyl groups and/or can have a heteroatom selected from O and S.

In the context of the present invention halogen is fluorine, chlorine, bromine or iodine and in particular fluorine, chlorine, or bromine.

The term "alkyl" includes straight-chain and branched alkyl groups. In this case, they are preferably straight-chain or branched $C_1$–$C_{12}$-alkyl groups, in particular $C_1$–$C_8$-alkyl groups, more preferably $C_1$–$C_6$-alkyl groups and particularly preferably $C_1$–$C_4$- or $C_1$–$C_3$-alkyl groups. Examples of alkyl groups are alkyl such as, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group defined as above, which is partially or completely halogenated by one or more halogen atoms, in particular fluorine or chlorine. Preferably, 1, 2 or 3 halogen atoms are present, the difluoromethane or the trifluoromethyl group being particularly preferred.

The above remarks regarding the alkyl group and haloalkyl group correspondingly apply to the alkyl and haloalkyl groups in alkoxy, haloalkoxy, alkylthio, haloalkylthio, alkylsulfinyl and alkylsulfonyl, etc.

The alkenyl group includes straight-chain and branched alkenyl groups. In this case, they are preferably straight-chain or branched $C_2$–$C_{12}$-alkenyl groups and in particular $C_2$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group can be partially or completely halogenated by one or more halogen atoms, in particular fluorine and chlorine. Preferably, it has 1, 2 or 3 halogen atoms.

The alkynyl group includes straight-chain or branched alkynyl groups. In this case, they are preferably straight-chain or branched $C_2$–$C_{12}$-alkynyl groups and in particular $C_2$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl2-butynyl, 1-ethyl-3-butynyl, 2-ethyl-3-butynyl and 1-ethyl-1-methyl-2-propynyl.

The above details regarding the alkenyl group and its halogen substituents and regarding the alkynyl group correspondingly apply to alkenyloxy and alkynyloxy.

The cycloalkyl group is preferably a $C_3$–$C_7$-cycloalkyl group, such as cyclopropyl, cyclobutyl, cyclopentyl or cyclohexyl. If the cycloalkyl group is substituted, it preferably has 1, 2 or 3 $C_1$–$C_4$-alkyl radicals as substituents. Cycloalkenyl is preferably a $C_4$–$C_7$-cycloalkenyl group, such as cyclobutenyl, cyclopentenyl or cyclohexenyl. If the cycloalkenyl group is substituted, it preferably has 1, 2 or 3 $C_1$–$C_4$-alkyl radicals as substituents.

The cycloalkoxy group is preferably a $C_5$–$C_6$-cycloalkoxy group, such as cyclopentyloxy or cyclohexyloxy. If the cycloalkoxy group is substituted, it preferably has 1, 2 or 3 $C_1$–$C_4$-alkyl radicals is as substituents.

The cycloalkenyloxy group is preferably a $C_5$–$C_6$-cycloalkenyloxy group, such as cyclopentenyloxy or cyclohexenyloxy. If the cycloalkenyloxy group is substituted, it preferably has 1, 2 or 3 $C_1$–$C_4$-alkyl radicals as substituents.

Bicycloalkyl is preferably decalinyl, indanyl, hydrindanyl, bornyl, pinanyl, caranyl, norbornyl and bicyclo[2.2.2]octanyl.

Bicycloalkenyl can have one or two double bonds and is preferably indenyl, pinenyl, norbornenyl and norbornadienyl.

Aryl is preferably phenyl.

Hetaryl is preferably a 5- or 6-membered aromatic heterocycle which has 1, 2 or 3 heteroatoms which independently of one another are selected from N, O and S. In this case, it is particularly pyridinyl, pyrimidinyl, thiazolyl, pyrazolyl, oxazolyl, isoxazolyl, isothiazolyl, imidazolyl, pyrrolyl, furanyl, thienyl or triazolyl.

Heterocyclyl is preferably a 5- or 6-membered, saturated or unsaturated heterocycle which has 1, 2 or 3 heteroatoms which independently of one another are selected from N, O and S. In this case, it is particularly the dihydro, tetrahydro and hexahydro derivatives of the radicals mentioned under "hetaryl". Pyrrolidinyl, tetrahydrofuranyl, imidazolidinyl, pyrazolidinyl, oxazolidinyl, isoxazolidinyl, thiazolidinyl, isothiazolidinyl, piperidinyl or morpholinyl are preferred.

If A in the formula II is a phenyl group, this can have one, two or three of the abovementioned substituents in any desired position. Preferably, these substituents are selected independently of one another from alkyl, difluoromethyl, trifluoromethyl and halogen, in particular chlorine, bromine and iodine. Particularly preferably, the phenyl group has one substituent in the 2-position.

If A is a 5-membered heterocycle, it is particularly a furyl, thiazolyl, pyrazolyl, imidazolyl, oxazolyl, thienyl, triazolyl or thiadiazolyl radical or the corresponding dihydro or tetrahydro derivatives thereof. A thiazolyl or pyrazolyl radical is preferred.

If A is a 6-membered heterocycle, in this case it is particularly a pyridyl radical or a radical of the formula:

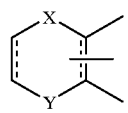

where one of the radicals X and Y is O, S or $NR^{20}$, $R^{20}$ being H or alkyl and the remainder of the radicals X and Y being $CH_2$, S, SO, $SO_2$ or $NR^{20}$. The dashed line means that, if appropriate, a double bond can be present.

Particularly preferably, the 6-membered aromatic heterocycle is a pyridyl radical, in particular a 3-pyridyl radical, or a radical of the formula:

(A3)

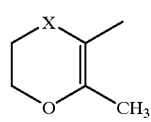

where X is $CH_2$, S, SO or $SO_2$.

The heterocyclic radicals mentioned can, if appropriate, have 1, 2 or 3 of the abovementioned substituents, these substituents preferably being selected independently of one another from alkyl, halogen, difluoromethyl or trifluoromethyl.

Particularly preferably, A is a radical of the formula:

(A1)

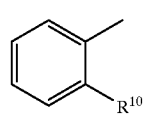

-continued

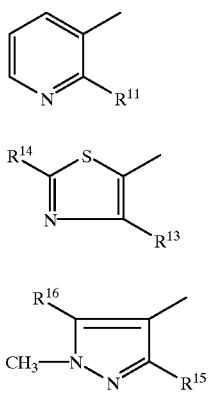

(A2)

(A5)

(A7)

where $R^{10}$, $R^{11}$, $R^{13}$, $R^{14}$, $R^{15}$ and $R^{16}$ independently of one another are hydrogen, alkyl, in particular methyl, halogen, in particular chlorine, $CHF_2$ or $CF_3$.

The radical $R^8$ in the formula II is preferably a hydrogen atom.

The radical $R^9$ in the formula II is preferably a phenyl radical. Preferably, $R^9$ has at least one substituent which is particularly preferably in the 2-position. Preferably, the substituent (or the substituents) is (are) selected from alkyl, cycloalkyl, cycloalkenyl, halogen or phenyl.

The substituents of the radical $R^9$, for their part, can in turn be substituted. The aliphatic or cycloaliphatic substituents can in this case be partially or completely halogenated, in particular fluorinated or chlorinated. Preferably, they have 1, 2 or 3 fluorine or chlorine atoms. If the substituent of the radical $R^9$ is a phenyl group, this can preferably be substituted by 1 to 3 halogen atoms, in particular chlorine atoms, and/or by a radical which is preferably selected from alkyl and alkoxy. The phenyl group is particularly preferably substituted by a halogen atom in the p-position, i.e. the particularly preferred substituent of the radical $R^9$ is a p-halosubstituted phenyl radical. The radical $R^9$ can also be fused to a saturated 5-membered ring, it being possible for this ring for its part to have 1 to 3 alkyl substituents. $R^9$ is then, for example, indanyl, thiaindanyl or oxaindanyl. Indanyl or 2-oxaindanyl, which are particularly bonded to the nitrogen atom via the 4-position, are preferred.

According to a preferred embodiment, the composition according to the invention contains as p-hydroxyaniline derivative a compound of the formula I where Z is hydrogen.

According to a further preferred embodiment, the composition according to the invention contains a compound of the formula I, where Z is hydrogen;

$R^1$ is alkyl, which can be partially or completely halogenated and/or can carry one or two of the following groups: alkoxy, haloalkoxy, cycloalkyl, cycloalkenyl, it being possible for the cyclic groups for their part to carry one, two or three halogen atoms and/or alkyl groups, and aryl, which can be partially or completely halogenated and/or can carry one, two or three of the following substituents: alkyl and haloalkyl;

cycloalkyl or cycloalkenyl, it being possible for these radicals to be partically or completely halogenated and/or to carry 1, 2, 3, 4 or 5 of the following groups: alkyl, haloalkyl and aryl, which can be partially or completely halogenated and/or can carry one, two or three of the following substituents: alkyl and haloalkyl;

$C_6$–$C_{15}$-bicycloalkyl or $C_7$–$C_{15}$-bicycloalkenyl, it being possible for these radicals to be partially or completely halogenated and/or to carry 1, 2, 3, 4 or 5 alkyl or haloalkyl groups;

$R^2$ and $R^3$ independently of one another are halogen, alkyl and haloalkyl.

According to a particularly preferred embodiment, the composition according to the invention contains a compound of the formula I, where:

Z is hydrogen;

$R^1$ is alkyl which can be partially or completely halogenated and/or can carry aryl, which for its part can be partially or completely halogenated and/or can carry alkyl;

cycloalkyl or cycloalkenyl, it being possible for these radicals to be partially or completely halogenated and to carry 1, 2, 3, 4 or 5 alkyl groups;

bicycloalkyl or bicycloalkenyl, it being possible for these radicals to be partially or completely halogenated and/or to carry 1, 2, 3, 4 or 5 alkyl groups;

$R^2$ and $R^3$ independently of one another are halogen, in particular fluorine or chlorine, or alkyl.

According to a particularly preferred embodiment, the composition according to the invention contains as p-hydroxyaniline derivative a compound of the formula I as in Table I.1.

TABLE I.1

Particularly preferred compounds of the formula I

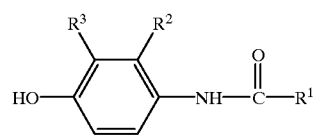

| No. | $R^3$ | $R^2$ | $R^1$ | Reference*) |
|---|---|---|---|---|
| I.1.1 | Cl | Cl | $C(CH_3)_2$—$CH_2$—⬡—$CH_3$ | (A), (C), (D) |
| I.1.2 | F | $CH_3$ | $C(CH_3)_2$—$CH_3$ | (A), (C), (D) |
| I.1.3 | F | $CH_3$ | $C(CH_3)_2$—$CH_2$—Cl | (A), (C), (D) |

TABLE I.1-continued

Particularly preferred compounds of the formula I

[Structure: HO-phenyl with R³, R² substituents, NH-C(=O)-R¹]

| No. | R³ | R² | R¹ | Reference*) |
|---|---|---|---|---|
| I.1.4 | F | CH₃ | C(CH₃)₂—CH₂—(phenyl)—Cl | (A), (C), (D) |
| I.1.5 | Cl | CH₃ | C(CH₃)₂—CH₂CH₂CH₃ | (A), (C), (D) |
| I.1.6 | F | CH₃ | C(CH₃)₂—CH₂CH₂CH₃ | (A), (C), (D) |
| I.1.7 | F | CH₃ | C(CH₃)₂—CH₂Br | (A), (C), (D) |
| I.1.8 | Cl | Cl | C(CH₃)₂—CH₃ | (A), (C), (D) |
| I.1.9 | Cl | Cl | C(CH₃)₂—CH₂Br | (A), (C), (D) |
| I.1.10 | Cl | CH₃ | C(CH₃)₂—CH₂Cl | (A), (C), (D) |
| I.1.11 | Cl | CH₃ | C(CH₃)₂—CH₂Br | (A), (C), (D) |
| I.1.12 | Cl | CH₃ | C(CH₃)₂—CH₃ | (A), (C), (D) |
| I.1.13 | Cl | CH₃ | C(CH₃)₂—CH₂—(phenyl)—Cl | (A), (C), (D, |
| I.1.14 | Cl | CH₃ | 2-CH₃-[2.2.1]heptan-2-yl | (B), (C), (D) |

*)(A) = EP-A 653 417
(B) = EP-A 653 418
(C) = German Patent Application file no. 195 04 599.8
(D) = German Patent Application file no. 195 40 970.1.

According to a specific embodiment, the composition according to the invention contains a compound of the formula I as in Table 1.2.

TABLE I.2

Particularly preferred compounds of the formula I
(Reference and formula as in Table I.1)

| No. | R³ | R² | R¹ | Reference |
|---|---|---|---|---|
| I.2.1 | Cl | Cl | C(CH₃)₂—CH₂Cl | (A), (C), (D) |
| I.2.2 | Cl | Cl | C(CH₃)₂—CH₂CH₃ | (A), (C), (D) |
| I.2.3 | Cl | Cl | C(CH₃)₂—CH₂CH₂CH₃ | (A), (C), (D) |
| I.2.4 | Cl | Cl | C(CH₃)₂—CH₂—(phenyl)—Cl | (A), (C), (D) |
| I.2.5 | Cl | Cl | 2-CH₃-[2.2.1]heptan-2-yl | (B), (C), (D) |
| I.2.6 | Cl | Cl | 2-CH₃-[2.2.1]hepten-2-yl | (B), (C), (D) |
| I.2.7 | Cl | Cl | 1-CH₃-cyclohexyl | EP-A 339 418 |

According to a further preferred embodiment, the composition according to the invention contains as amide compound a compound of the formula II, where A has the following meanings:
phenyl, pyridyl, dihydropyranyl, dihydrooxathiinyl, dihydrooxathiinyl oxide, dihydrooxathiinyl dioxide, furyl, thiazolyl, pyrazolyl or oxazolyl, it being possible for these groups to have 1, 2 or 3 substituents which independently of one another are selected from alkyl, halogen, difluoromethyl and trifluoromethyl.

According to a further preferred embodiment A is:
pyridin-3-yl, which is unsubstituted or substituted in the 2-position by halogen, methyl, difluoromethyl, trifluoromethyl, methoxy, methylthio, methylsulfinyl or methylsulfonyl;
phenyl which is unsubstituted or substituted in the 2-position by methyl, trifluoromethyl, chlorine, bromine or iodine;
2-methyl-5,6-dihydropyran-3-yl;
2-methyl-5,6-dihydro-1,4-oxathiin-3-yl or the 4-oxide or 4,4-dioxide thereof;
2-methylfuran-3-yl, which is unsubstituted or substituted in the 4- and/or 5-position by methyl;
thiazol-5-yl, which is unsubstituted or substituted in the 2- and/or 4-position by methyl, chlorine, difluoromethyl or trifluoromethyl;
thiazol-4-yl, which is unsubstituted or substituted in the 2- and/or 5-position by methyl, chlorine, difluoromethyl or trifluoromethyl;
1-methylpyrazol-4-yl, which is unsubstituted or substituted in the 3- and/or 5-position by methyl, chlorine, difluoromethyl or trifluoromethyl; or
oxazol-5-yl, which is unsubstituted or substituted in the 2- and/or 4-position by methyl or chlorine.

According to a further preferred embodiment, the compositions according to the invention contain as amide compound a compound of the formula II, where $R^9$ is a phenyl group which is unsubstituted or substituted by 1, 2 or 3 of the abovementioned substituents.

According to a further preferred embodiment, the compositions according to the invention contain as amide compound a compound of the formula II, where $R^9$ is a phenyl group which in the 2-position has one of the following substituents:

$C_3$–$C_6$-alkyl, $C_5$–$C_6$-cycloalkenyl, $C_5$–$C_6$-cycloalkyloxy, $C_5$–$C_6$-cycloalkenyloxy, it being possible for these groups to be substituted by 1, 2 or 3 $C_1$–$C_4$-alkyl groups, phenyl, which is substituted by 1 to 5 halogen atoms and/or 1 to 3 groups which independently of one another are selected from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, indanyl or oxaindanyl, which is unsubstituted or substituted by 1, 2 or 3 $C_1$–$C_4$-alkyl groups.

According to a further preferred embodiment, the compositions according to the invention contain as amide compound a compound of the formula IIa,

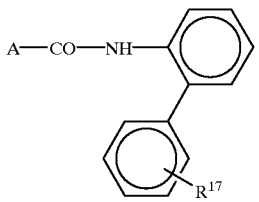

(IIa)

where

A is

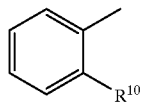

(A1)

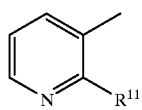

(A2)

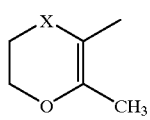

(A3)

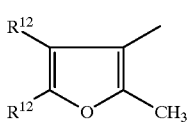

(A4)

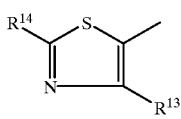

(A5)

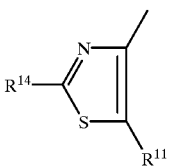

(A6)

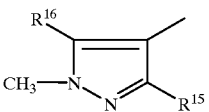

(A7)

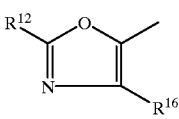

(A8)

X is methylene, sulfur, sulfinyl or sulfonyl ($SO_2$), $R^{10}$ is methyl, difluoromethyl, trifluoromethyl, chlorine, bromine or iodine, $R^{11}$ is trifluoromethyl or chlorine, $R^{12}$ is hydrogen or methyl, $R^{13}$ is methyl, difluoromethyl, trifluoromethyl or chlorine, $R^{14}$ is hydrogen, methyl or chlorine, $R^{15}$ is methyl, difluoromethyl or trifluoromethyl, $R^{16}$ is hydrogen, methyl, difluoromethyl, trifluoromethyl or chlorine, $R^{17}$ is $C_1$–$C_4$-alkyl, $C_1$–$C_4$-alkoxy, $C_1$–$C_4$-alkylthio or halogen.

According to a particularly preferred embodiment, the compositions contain as amide compound a compound of the formula IIb

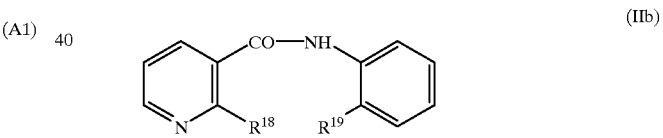

(IIb)

where $R^{18}$ is halogen and $R^{19}$ is phenyl which is substituted by halogen.

Amide compounds which can be used are mentioned in EP-A-545 099 and 589 301, to which reference is entirely made hereby.

The preparation of the amide compounds of the formula II is disclosed, for example, in EP-A-545 099 or 589 301 or can be carried out by similar processes.

In order to display synergistic action, the active compounds I and II are customarily employed in a weight ratio which is in the range from 20:1 to 1:20, preferably 10:1 to 1:5, in particular 3:1 to 1:1.

The invention also relates to a method of controlling harmful fungi, which comprises treating the fungi, their habitat or the materials, plants, seeds, soils, surfaces or spaces to be protected from fungal attack with a composition as defined above, it being possible for the active compounds to be applied simultaneously, to be precise together or separately, or in succession.

The compositions according to the invention can be applied by spraying, atomizing, dusting, broadcasting or watering, for example in the form of directly sprayable solutions, powders, suspensions, even high-percentage aqueous, oily or other suspensions, or dispersions, emulsions, oil dispersions, pastes, dusting compositions, broadcasting compositions, or granules. The application forms depend on the intended uses: they should in any case guarantee the finest possible distribution of the active compounds according to the invention.

Normally, the plants are sprayed or dusted with the active compounds or the seeds of the plants are treated with the active compounds.

The formulations are prepared in a known manner, e.g. by extending the active compound using solvents and/or carriers, if desired using emulsifiers and dispersants, it being possible if water is used as a diluent also to use other organic solvents as auxiliary solvents. Suitable auxiliaries for this are in the main: solvents such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers such as ground natural minerals (e.g. kaolins, aluminas, talc, chalk) and ground synthetic minerals (e.g. highly disperse silicic acid, silicates); emulsifiers such as nonionic and anionic emulsifiers (e.g. polyoxyethylene-fatty alcohol-ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, e.g. lignosulfonic, phenolsulfonic, napthalene-sulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols, and also fatty alcohol glycol ethers, condensation products of sulfonated napthalene and its derivatives with formaldehyde, condensation products of naphthalene or of the naphthalenesulfonic acids with phenol and formaldehyde, polyoxyethylene octylphenyl ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground synthetic materials, fertilizers, such as ammonium sulfate, ammonium phosphate, ammonium nitrate, ureas and vegetable products, such as cereal flour, tree bark, wood and nutshell meal, cellulose powder or other solid carriers.

Examples of such preparations which contain the active compounds in a weight ratio of 1:1 are:

I. a solution of 90 parts by weight of the active compounds and 10 parts by weight of N-methylpyrrolidone, which is suitable for application in the form of very small drops;

II. a mixture of 20 parts by weight of the active compounds, 80 parts by weight of xylene, 10 parts by weight of the addition product of from 8 to 10 mol of ethyleneoxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; by finely dispersing the solution in water a dispersion is obtained;

III. an aqueous dispersion of 20 parts by weight of the active compounds, 40 parts by weight of cyclohexanone, 30 parts by weight of isobutanol, 20 parts by weight of the addition products of 40 mol of ethylene oxide to 1 mol of castor oil;

IV. an aqueous dispersion of 20 parts by weight of the active compounds, 25 parts by weight of cyclohexanol, 65 parts by weight of a mineral oil fraction of boiling point 210 to 280° C. and 10 parts by weight of the addition product of 40 mol of ethylene oxide to 1 mol of castor oil;

V. a mixture, ground in a hammer mill, of 80 parts by weight of the active compounds, 3 parts by weight of the sodium salt of diisobutylnapthalene-1-sulfonic acid, 10 parts by weight of the sodium salt of a lignosulfonic acid from a sulfite waste liquor and 7 parts by weight of powdered silica gel; by finely dispersing the mixture in water a spray mixture is obtained;

VI. an intimate mixture of 3 parts by weight of the active compounds and 97 parts by weight of finely divided kaolin; this dusting composition contains 3% by weight of active compound;

VII. an intimate mixture of 30 parts by weight of the active compounds, 92 parts by weight of powdered silica gel and 8 parts by weight of paraffin oil, which has been sprayed onto the surface of the silica gel; this preparation gives the active compounds a good adherence;

VIII. a stable aqueous dispersion of 40 parts by weight of the active compounds, 10 parts by weight of the sodium salt of a phenolsulfonic acid-urea-formaldehyde condensate, 2 parts by weight of silica gel and 48 parts by weight of water, which can be further diluted;

IX. a stable oily dispersion of 20 parts by weight of the active compounds, 2 parts by weight of the calcium salt of dodecylbenzenesulfonic acid, 8 parts by weight of fatty alcohol polyglycol ether, 20 parts by weight of the sodium salt of a phenolsulfonic acid-urea-formaldehyde condensate and 88 parts by weight of a paraffinic mineral oil.

The compositions according to the invention are distinguished by an outstanding activity against a broad spectrum of phytopathogenic fungi, in particular against Botrytis. In some cases they are systemically active (i.e. they can be absorbed by the treated plants without loss of action and, if appropriate, transported in the plants) and can be employed as foliar and soil fungicides.

They are of particular importance for the control of a multiplicity of fungi on various crop plants such as wheat, rye, barley, vines, rice, corn, grass, cotton, soybeans, coffee, sugar cane, votes, fruits and decorative plants and vegetable plants such as cucumbers, beans and cucurbits, and on the seeds of these plants.

The compositions are applied by treating the fungi or the seeds, plants, materials or the soil to be protected from fungal attack with a fungicidally active amount of the active compounds.

Application is carried out before or after the infection of the materials, plants or seeds by the fungi.

The compositions are especially suitable for controlling the following plant diseases:
*Erysipe graminis* (powdery mildew) in cereals,
*Erysiphe cichoracearum* and *Sphaerotheca fuliginea* on cucurbits,
*Podosphaera leucotricha* on apples,
*Uncinula necator* on vines,
*Venturia inaequalis* (scab) on apples,
Helminthosporium species on cereals,
*Septoria nodorum* on wheat,
*Botrytis cinerea* (grey mold) on strawberries, vines;
*Cercospora arachidicola* on groundnuts,
*Pseudocercosporella herpotrichoides* on wheat, barley,
*Pyricularia oryzae* on rice,
Fusarium and Verticillium species on various plants,
Alternaria species on vegetables and fruit,
Monilinia species in fruit,
Sclerotinia species in rape and vegetables.

Application against Botrytis is preferred.

The compositions can also be employed in material protection (wood preservation), e.g. against *Paecilomyces variotii*.

The fungicidal compositions in general contain from 0.1 to 95, preferably from 0.5 to 90, % by weight of active compound.

The application rates, depending on the effect desired, are from 0.02 to 3 kg of active compound per ha.

In the treatment of seed, in general amounts of active compound of from 0.001 to 50 g, preferably 0.01 to 10 g, are needed per kilogram of seed.

In the application form as fungicides, the compositions according to the invention can also contain other active compounds, e.g. herbicides, insecticides, growth regulators, fungicides or alternatively fertilizers.

On mixing with fungicides, in many cases an increase in the fungicidal spectrum of action is obtained here.

The following list of fungicides with which the compounds according to the invention can be applied together is intended to illustrate the combination possibilities, but not to restrict them:

sulfur,
dithiocarbonates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediamine-bis-dithiocarbamate,
tetramethylthiuram disulfide,
ammonia complex of zinc (N,N-ethylene-bis-dithiocarbamate),
ammonia complex of zinc (N,N-propylene-bis-dithiocarbamate),
zinc (N,N'-propylene-bis-dithiocarbamate),
N,N'-polypropylene-bis(thiocarbamoyl) disulfide,
nitro derivatives, such as
dinitro(1-methylheptyl)phenyl crotonate,
2-sec-butyl-4,6-dinitrophenyl 3,3-dimethylacrylate,
2-sec-butyl-4,6-dinitrophenyl isopropyl carbonate,
diisopropyl 5-nitroisophalate;
heterocyclic substances, such as
2-heptadecyl-2-imidazoline acetate,
2,4-dichloro-6-(o-chloroanilino)-s-triazine,
O,O-diethyl phthalimidophosphonothioate,
5-amino-1-β-[bis(dimethylamino)phosphynyl]-3-phenyl-1,2,4-triazole,
2,3-dicyano-1,4-dithioanthraquinone,
2-thio-1,3-dithiolo-β-[4,5-b]quinoxaline,
methyl 1-(butylcarbamoyl)-2-benzimidazole carbamate,
2-methoxycarbonylaminobenzimidazole,
2-(fur-2-yl)benzimidazole,
2-(thiazol-4-yl)benzimidazole,
N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfamide,
5-ethoxy-3-trichloromethyl-1,2,3-thiadiazole,
2-thiocyanatomethylbenzothiazole,
1,4-dichloro-2,5-dimethoxybenzene,
4-(2-chlorophenylhydrazono)-3-methyl-5-isoxazolone,
2-thiopyridine-1-oxide,
8-hydroxyquinoline or its copper salt,
2,3-dihydro-5-carboxanilido-6-methyl-1,4-oxathiin,
2,3-dihydro-5-carboxanilido-6-methyl-1,4-oxathiin-4,4-dioxide,
2-methyl-5,6-dihydro-4H-pyran-3-carboxanilide,
2-methyl-furan-3-carboxanilide,
2,5-dimethyl-furan-3-carboxanilide,
2,4,5-trimethyl-furan-3-carboxanilide,
2,5-dimethyl-furan-3-carboxylic acid cyclohexylamide,
N-cyclohexyl-N-methoxy-2,5-dimethyl-furan-3-carboxamide,
2-methylbenzanilide,
2-iodobenzanilide,
N-formyl-N-morpholine-2,2,2-trichloroethyl acetate,
piperazine-1,4-diylbis(1-(2,2,2-trichloroethyl))formamide,
1-(3,4-dichloroanilino)-1-formylamino-2,2,2-trichloroethane,
2,6-dimethyl-N-tridecylmorpholine or its salts,
2,6-dimethyl-N-cyclododecylmorpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-yl-ethyl]-1H-1,2,4-triazole
1-[2-(2,4-dichlorophenyl)-4-n-propyl)-1,3-dioxolan-2-yl-ethyl]-1H-1,2,4-triazole
N-(n-propyl)-N-(2,4,6-trichlorophenoxyethyl)-N'-imidazolyl urea,
1-(4-chlorophenoxy)-3,3-dimethyl-1-(1H-1,2,4-triazol-1-yl)-2-butanone, 1-(4-chlorophenyl)-3,3-dimethyl)-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis (p-chlorophenyl)-3-pyridinemethanol,
1,2-bis(3-ethoxycarbonyl-2-thioureido)benzene,
1,2-bis(3-methoxycarbonyl-2-thioureido)benzene, and various fungicides, such as
dodecylguanidine acetate,
3-[3-(3,5-dimethyl)-2-oxycyclohexyl-2-hydroxyethyl] glutarimide,
hexachlorobenzene,
DL-methyl-N-(2,6-dimethylphenyl)-N-2-furoyl alaninate,
DL-N-(2,6-dimethylphenyl)-N-(2'-methoxyacetyl)alanine methyl ester,
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-(3,5-dichlorophenyl)-5-methyl-5-methoxymethyl-1,3-oxazolidine-2,4-dione, 3-(3,5-dichlorophenyl)-1-isopropylcarbamoylhydantoin,
N-(3,5-dichlorophenyl)-1,2-dimethylcyclopropane-1,2-dicarboximide,
2-cyano-[N-ethylaminocarbonyl-2-methoximino]acetamide
1-[2-(2,4-dichlorophenyl)pentyl]-1H-1,2,4-triazole,
2,4-difluoro-α-(1H-1,2,4-triazol-1-ylmethyl)benzhydryl alcohol,
N-(3-chloro-2,6-dinitro-4-trifluoromethylphenyl)-5-trifluoromethyl-3-chloro-2-aminopyridine,
1-((bis(4-fluorophenyl)methylsilyl)methyl-1H-1,2,4-triazole,
[2-(4-chlorophenyl)ethyl](1,1-dimethylethyl)1H-1,2,4-triazole-1-ethanol, 1-[3-(2-chlorophenyl)-1-(4-fluorophenyl)oxiran-2-yl-methyl]-1H-1,2,4-triazole,
strobilurins such as methyl E-methoximino-[α-(o-tolyloxy)-o-tolyl]acetate, methyl E-2-{2-[6-(2-cyanophenoxy)pyrimidin-4-yl-oxy]phenyl}-3-methoxyacrylate, methyl E-methoximino-[α-(2,5-dimethyloxy)-o-tolyl]acetamide,
anilinopyrimidines such as N-(4,6-dimethylpyrimidin-2-yl) aniline,
N-[4-methyl-6-(1-propynyl)pyrimidin-2-yl]aniline,
N-(4-methyl-6-cyclopropylpyrimidin-2-yl)aniline,
phenylpyrroles such as 4-(2,2-difluoro-1,3-benzodioxol-4-yl)-pyrrole-3-carbonitrile,
cinnamides such as
3-(4-chlorophenyl)-3-(3,4-dimethoxyphenyl)acrylic acid morpholide.

MODE(S) FOR CARRYING OUT THE INVENTION

The synergistic action of the compositions according to the invention is illustrated with the aid of the following use examples, the active compounds I used being the compounds of the formulae I.2.1, I.2.5 and I.2.7 as in Table I.2

I.2.1

I.2.5

I.2.7 and the amide compound used being the compound of the formula II.1

II.1

II.1

USE EXAMPLE 1

Activity Against *Botrytis Cinerea*

Paprika seedlings of the variety "Neusiedler Ideal Elite" were sprayed until dripping wet, after 4 to 5 leaves had developed well, with aqueous suspensions, which contained 80% of active compound and 20% of emulsifier in the dry matter. After the spray coating had dried on, the plants were sprayed with a conidia suspension of the fungus Botrytis cinerea and placed in a chamber with high atmospheric humidity at 22 to 24° C. After 5 days, the disease had developed on the untreated control plants so severely that the resulting leaf necrosis covered the greater part of the leaves (attack 100%).

The visually determined values for the percentage proportion of affected leaf area were converted into efficiencies as % of the untreated control. Efficiency 0 is equal to attack as in the untreated control, efficiency 100 is 0% attack. The efficiencies to be expected for active compound combinations were determined by the Colby formula (S. R. Colby "Calculating synergistic and antagonistic responses of herbicide combinations", Weeds 15, pages 20 to 22 (1967) and compared with the observed efficiencies. The results are indicated in Table 1 which follows.

TABLE 1

| Active compound | Active compound concentration in ppm | Efficiency in % of the control | |
|---|---|---|---|
| | | observed | calculated* |
| control (untreated) | — | — | 0 | — |
| II.1 | — | 100 | 0 | — |
| | — | 25 | 0 | — |
| I.2.1 | 25 | — | 40 | — |
| I.2.5 | 100 | — | 80 | — |
| | 25 | — | 65 | — |
| I.2.7 | 100 | — | 70 | — |
| | 25 | — | 35 | — |
| I.2.1 + II.1 | 25 | 25 | 84 | 40 |
| I.2.5 + II.1 | 100 | 25 | 99 | 80 |
| | 25 | 25 | 99 | 65 |
| I.2.7 + II.1 | 100 | 25 | 98 | 70 |
| | 25 | 25 | 98 | 35 |

*calculated according to the Colby formula

From the results of the test, it emerges that the observed efficiency in all mixing ratios is higher than the efficiency precalculated according to the Colby formula, i.e. a synergistic effect is present.

USE EXAMPLE 2

Activity Against Botrytis Cinerea on Peppers

Slices of green peppers were sprayed with an aqueous active compound preparation which contained 80% of active compound and 20% of emulsifier in the dry matter until dripping wet. 2 hours after the spray coating had dried on, the fruit slices were inoculated with a spore suspension of Botrytis cinerea, which contained $1.7 \times 10^6$ spores per ml of a 2% strength biomalt solution. The inoculated fruit slices were then incubated in humid chambers at 18° C. for 4 days. The development of Botrytis on the attacked fruit slices was then assessed visually (100% attack).

The visually determined values for the percentage proportion of attacked leaf area were converted into efficiencies as % of the untreated control. Efficiency 0 is equal to attack as in the untreated control, efficiency 100 is 0% attack. The efficiencies to be expected for active compound combinations were determined by the Colby formula (Colby, S. R. "Calculating synergistic and antagonistic responses of herbicide combinations", Weeds, 15, pp. 20 to 22, 1967) and compared with the observed efficiencies. The results are indicated in Table 2 which follows.

TABLE 2

| Active compound | Active compound concentration in ppm | Efficiency in % of the control | |
|---|---|---|---|
| | | observed | calculated* |
| control (untreated) | — | — | 0 | — |
| II.1 | — | 25 | 50 | — |
| I.2.1 | 100 | — | 20 | — |
| | 25 | — | 10 | — |
| I.2.5 | 25 | — | 10 | — |
| I.2.7 | 100 | — | 25 | — |
| I.2.1 + II.1 | 100 | 25 | 90 | 60 |
| | 25 | 25 | 87 | 55 |

TABLE 2-continued

| Active compound | Active compound concentration in ppm | Efficiency in % of the control | |
|---|---|---|---|
| | | observed | calculated* |
| I.2.5 + II.1 | 25 | 25 | 65 | 55 |
| I.2.7 + II.1 | 100 | 25 | 74 | 63 |

*calculated according to the Colby formula

From the results of the test, it emerges that the observed efficiency in all mixing ratios is higher than the efficiency precalculated according to the Colby formula, i.e. a synergistic effect is present.

We claim:

1. A composition for controlling harmful fungi, comprising a solid or liquid carrier and synergistically effective amounts of
   a) at least one p-hydroxyaniline of formula I

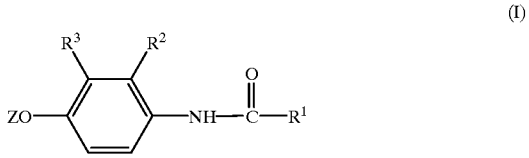

(I)

wherein
   $R^1$ is cycloalkyl or cycloalkenyl, wherein these radicals are unsubstituted, partially or completely halogenated and/or carry 1, 2, 3, 4 or 5 of the following groups: alkyl, haloalkyl, alkoxy, haloalkoxy and aryl, which can be partially or completely halogenated and/or can carry one, two or three of the following substituents: nitro, cyano, alkyl, haloalkyl, alkoxy, haloalkoxy and alkylthio;
   $R^2$ and $R^3$ independently of one another are halogen, alkyl, haloalkyl, alkoxy or haloalkoxy;
   Z is H, and
   b) at least one amide compound of formula II

A—CO—NR$^8$—R$^9$      (II)

wherein
   A is 3-pyridyl which may have 1, 2 or 3 substituents which are selected independently of one another from the group consisting of alkyl, halogen, $CHF_2$, and $CF_3$;
   $R^8$ is a hydrogen atom, alkyl or alkoxy;
   $R^9$ is a 2-biphenyl group, which is substituted by 1 to 5 halogen atoms and/or 1 to 3 groups which independently of one another are selected from the group consisting of $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio.

2. The composition defined in claim 1, wherein
   $R^1$ is cycloalkyl or cycloalkenyl, wherein these radicals are unsubstituted, partially or completely halogenated and/or carry 1, 2, 3, 4 or 5 of the following groups: alkyl, haloalkyl and aryl, which can be partially or completely halogenated and/or can carry one, two or three of the following substituents: alkyl and haloalkyl;
   $R^2$ and $R^3$ independently of one another are halogen, alkyl and haloalkyl.

3. The composition defined in claim 2, wherein
   $R^1$ is cycloalkyl or cycloalkenyl, wherein these radicals are unsubstituted, partially or completely halogenated and/or carry 1, 2, 3, 4 or 5 alkyl groups;
   $R^2$ and $R^3$ independently of one another are halogen or alkyl.
4. The composition defined in claim 3, wherein $R^2$ and $R^3$ independently of one another are fluorine, chlorine or alkyl.
5. The composition defined in claim 1, wherein $R^1$ is 1-methylcyclohexyl, and $R^2$ and $R^3$ are each chlorine.
6. The composition defined in claim 1, wherein A is 3-pyridyl, which is unsubstituted or substituted in the 2-position by halogen, methyl, difluoromethyl, or trifluoromethyl.
7. The composition defined in claim 1, comprising components (a) and (b) in a weight ratio of from 20:1 to 1:20.
8. The composition defined in claim 1, comprising components (a) and (b) in a weight ratio of from 10:1 to 1:5.
9. The composition defined in claim 1, comprising components (a) and (b) in a weight ratio of from 3:1 to 1:1.
10. The composition defined in claim 1, which is formulated in two parts, one part comprising the hydroxyaniline of formula I in a solid or liquid carrier and the other part comprising the amide compound of formula II in a solid or liquid carrier.
11. A method of controlling harmful fungi, which comprises treating the fungi, their habitat or the materials, plants, seeds, soils, surfaces or spaces to be protected from fungal attack with the composition defined in claim 1, wherein components (a) and (b) are applied simultaneously or in succession.
12. The method of claim 11, wherein
    $R^1$ is cycloalkyl or cycloalkenyl, wherein these radicals are unsubstituted, partially or completely halogenated and/or carry 1, 2, 3, 4 or 5 alkyl groups;
    $R^2$ and $R^3$ independently of one another are halogen or alkyl.
13. The method of claim 11, wherein A is 3-pyridyl, which is unsubstituted or substituted in the 2-position by halogen, methyl, difluoromethyl, or trifluoromethyl.
14. The method of claim 11, wherein components (a) and (b) of the composition are applied in a weight ratio of from 20:1 to 1:20.
15. The method of claim 11, wherein components (a) and (b) of the composition are applied in a weight ratio of from 10:1 to 1:5.
16. The method of claim 11, wherein components (a) and (b) of the composition are applied in a weight ratio of from 3:1 to 1:1.
17. A composition for controlling harmful fungi, comprising a solid or liquid carrier and synergistically effective amounts of
    a) at least one p-hydroxyaniline of formula I

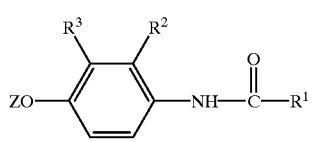

(I)

wherein
    $R^1$ is cycloalkyl or cycloalkenyl, wherein these radicals are unsubstituted, partially or completely halogenated and/or carry 1, 2, 3, 4 or 5 of the following groups: alkyl, haloalkyl, alkoxy, haloalkoxy and aryl, which can be partially or completely halogenated and/or can carry one, two or three of the following substituents: nitro, cyano, alkyl, haloalkyl, alkoxy, haloalkoxy and alkylthio;
    $R^2$ and $R^3$ independently of one another are halogen, alkyl, haloalkyl, alkoxy or haloalkoxy;
    Z is H, and
b) at least one amide compound of formula IIa

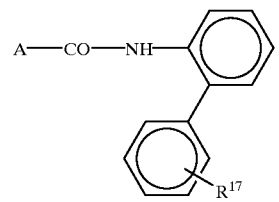

(IIa)

wherein A is a radical A2

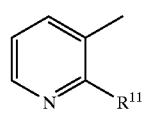

(A2)

wherein $R^{11}$ is trifluoromethyl or chlorine, and $R^{17}$ is $C_1$–$C_4$-alkyl, $C_1$–$C_4$-alkoxy, $C_1$–$C_4$-alkylthio or halogen.
18. A composition for controlling harmful fungi, comprising a solid or liquid carrier and synergistically effective amounts of
    a) at least one p-hydroxyaniline of formula I

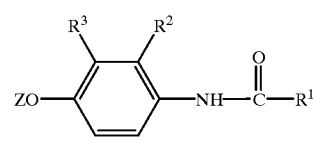

(I)

wherein
    $R^1$ is cycloalkyl or cycloalkenyl, wherein these radicals are unsubstituted, partially or completely halogenated and/or carry 1, 2, 3, 4 or 5 of the following groups: alkyl, haloalkyl, alkoxy, haloalkoxy and aryl, which can be partially or completely halogenated and/or can carry one, two or three of the following substituents: nitro, cyano, alkyl, haloalkyl, alkoxy, haloalkoxy and alkylthio;
    $R^2$ and $R^3$ independently of one another are halogen, alkyl, haloalkyl, alkoxy or haloalkoxy;
    Z is H, and
b) at least one amide compound of formula IIb

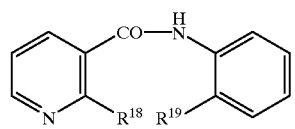

(IIb)

wherein $R^{18}$ is halogen and $R^{19}$ is phenyl which is substituted by halogen.

19. A composition for controlling harmful fungi, comprising a solid or liquid carrier and synergistically effective amounts of a) at least one p-hydroxyaniline of formula I

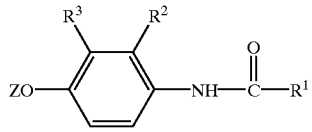

(I)

wherein

R$^1$ is cycloalkyl or cycloalkenyl, wherein these radicals are unsubstituted, partially or completely halogenated and/or carry 1, 2, 3, 4 or 5 of the following groups: alkyl, haloalkyl, alkoxy, haloalkoxy and aryl, which can be partially or completely halogenated and/or can carry one. two or three of the following substituents: nitro, cyano, alkyl, haloalkyl, alkoxy, haloalkoxy and alkylthio;

R$^2$ and R$^3$ independently of one another are halogen, alkyl, haloalkyl, alkoxy or haloalkoxy;

Z is H, and b) at least one amide compound of formula

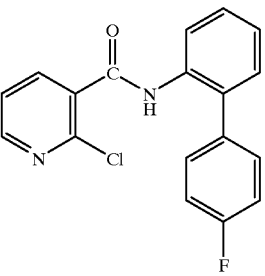

or

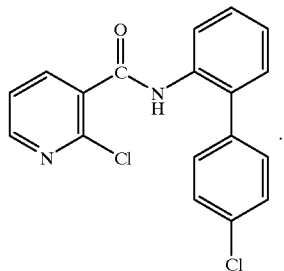

* * * * *